US010876990B2

(12) United States Patent
Banks

(10) Patent No.: US 10,876,990 B2
(45) Date of Patent: Dec. 29, 2020

(54) ELECTROCHEMICAL SENSOR AND METHOD OF USING SAME

(71) Applicant: Ecolab USA Inc., St. Paul, MN (US)

(72) Inventor: Rodney H. Banks, Aurora, IL (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 16/415,403

(22) Filed: May 17, 2019

(65) Prior Publication Data
US 2019/0277792 A1 Sep. 12, 2019

Related U.S. Application Data

(62) Division of application No. 15/668,363, filed on Aug. 3, 2017, now Pat. No. 10,295,492, which is a division
(Continued)

(51) Int. Cl.
*G01N 27/30* (2006.01)
*G01N 25/00* (2006.01)
(Continued)

(52) U.S. Cl.
CPC ............ *G01N 27/30* (2013.01); *G01N 25/00* (2013.01); *G01N 27/06* (2013.01); *G01N 27/403* (2013.01);
(Continued)

(58) Field of Classification Search
None
See application file for complete search history.

(56) References Cited

U.S. PATENT DOCUMENTS

| 3,939,408 A | 2/1976 | Brown |
| 4,118,663 A | 10/1978 | Barben |
| (Continued) | | |

FOREIGN PATENT DOCUMENTS

| CA | 1227247 A1 | 9/1987 |
| CA | 1253205 A1 | 4/1989 |
| (Continued) | | |

OTHER PUBLICATIONS

International Search Report and Written Opinion for International Application No. PCT/US2015/011917, dated Apr. 30, 2015, 16 pages.
(Continued)

*Primary Examiner* — Erica S Lin
(74) *Attorney, Agent, or Firm* — Fredrikson & Byron P.A.

(57) ABSTRACT

Methods for analyzing a fluid sample can include providing a sensor comprising a non-conductive housing and having a first face and an electrode array mounted in the first face. The method can include disposing the first face of the housing into a fluid sample to be analyzed, selecting a mode of operation, and initiating sensor operation. Modes of operation can include electrochemical operation and conductivity analysis, and can be selected via positioning a switch. The method can include receiving information from the sensor regarding at least one parameter of the fluid. Such parameters can include a concentration of a target constituent in the fluid sample, combined concentrations of different species within the fluid sample, and/or information indicative of the conductivity of the fluid sample.

18 Claims, 13 Drawing Sheets

Related U.S. Application Data of application No. 14/166,513, filed on Jan. 28, 2014, now Pat. No. 9,726,627.

(51) Int. Cl.
*G16C 99/00* (2019.01)
*G01N 27/06* (2006.01)
*G01N 33/18* (2006.01)
*G01N 27/403* (2006.01)
*A61L 2/28* (2006.01)
*C01B 11/06* (2006.01)
*C01B 15/00* (2006.01)
*C07C 409/00* (2006.01)

(52) U.S. Cl.
CPC ............. *G01N 33/18* (2013.01); *G16C 99/00* (2019.02); *A61L 2/28* (2013.01); *C01B 11/06* (2013.01); *C01B 15/00* (2013.01); *C07C 409/00* (2013.01)

(56) References Cited

U.S. PATENT DOCUMENTS

| | | | |
|---|---|---|---|
| 4,332,658 A | 6/1982 | Tsuboshima et al. | |
| 4,656,427 A | 4/1987 | Dauphinee | |
| 4,672,322 A | 6/1987 | Gratteau et al. | |
| 4,682,113 A | 7/1987 | Barben, II et al. | |
| 5,305,214 A | 4/1994 | Komatsu | |
| 5,438,271 A | 8/1995 | White et al. | |
| 7,259,566 B2 | 8/2007 | Broadbent et al. | |
| 2003/0232450 A1 | 12/2003 | Yoshida | |
| 2004/0079686 A1 | 4/2004 | Moscaritolo et al. | |
| 2005/0016847 A1* | 1/2005 | Buehler | G01N 27/4035 204/412 |
| 2006/0037393 A1 | 2/2006 | Itakura et al. | |
| 2006/0062734 A1 | 3/2006 | Melker et al. | |
| 2007/0018652 A1 | 1/2007 | Broadbent et al. | |
| 2008/0099331 A1 | 5/2008 | Hsiung et al. | |
| 2011/0089957 A1 | 4/2011 | Sheppard, Jr. | |
| 2011/0230735 A1 | 9/2011 | Wolfe et al. | |
| 2012/0097554 A1* | 4/2012 | Shah | A61B 5/1473 205/782 |
| 2012/0132540 A1* | 5/2012 | Wang | A61B 5/14532 205/775 |
| 2013/0003048 A1 | 1/2013 | Caussin De Schneck et al. | |
| 2013/0316340 A1* | 11/2013 | Kelley | G01N 33/5438 435/6.11 |

FOREIGN PATENT DOCUMENTS

| | | |
|---|---|---|
| CA | 2598664 A1 | 8/2006 |
| EP | 231609 A2 | 8/1987 |
| WO | 2006091607 A2 | 8/2006 |

OTHER PUBLICATIONS

Li et al., "A High-Performance Measurement System for Conductivity Sensors," Conductivity Measurement Setup, Version 0.1, Jun. 2005, 2 pages.

* cited by examiner

ELECTROCHEMICAL SENSOR AND METHOD OF USING SAME

CROSS-REFERENCES

This application is a divisional of U.S. application Ser. No. 15/668,363, filed Aug. 3, 2017 which is a divisional of U.S. application Ser. No. 14/166,513, filed Jan. 28, 2014 which issued as U.S. Pat. No. 9,726,267 on Aug. 8, 2017, the content of which are hereby incorporated by reference in their entirety.

TECHNICAL FIELD

This disclosure relates generally to electrical measuring devices and, more particularly, to multi-electrode probes and other integrated sensors for monitoring the concentration of one or more substances in a sample.

BACKGROUND

In cleaning and antimicrobial operations, commercial users (e.g., restaurants, hotels, food and beverage plants, grocery stores, etc.) rely upon the concentration of a cleaning or antimicrobial product to make the product work effectively. Failure of a cleaning or antimicrobial product to work effectively (for example due to concentration issues) can cause a commercial user to perceive the product as lower quality. End consumers may also perceive the commercial provider of such products as providing inferior services. In addition, commercial users may be investigated and/or sanctioned by government regulatory and health agencies. Accordingly, there is a need for a system that can monitor the characteristics of fluid solutions, e.g., to determine if the concentration of a product is within a specified concentration range. The same may be true for other applications, such as commercial and industrial water treatment, pest control, beverage and bottling operations, oil and gas refining and processing operations, and the like.

One method of monitoring the concentration of a product relies on electroanalytical methods to measure various parameters of the product. One such parameter can be the conductivity of the product. Some existing conductivity sensors comprise two electrodes, and operate by applying a voltage across the two electrodes and measuring a resulting current. The relationship between the magnitudes of the current and the voltage allow the resistance and therefore conductivity of the product to be determined. Such two-electrode designs can result in fouling effects at the electrodes and/or narrow ranges of operation.

More expensive four-electrode devices have been used to overcome some of the shortcomings of the two-electrode designs. Exemplary four-electrode devices can pass a current from one electrode to another to maintain a certain voltage between two separate electrodes. Other devices pass a known current between two of the electrodes and measure the voltage difference between the other two electrodes. One disadvantage of such designs, however, is that in some cases, such as in the case of high product resistance, the device must apply an undesirably high voltage in order to achieve an appropriate current. High voltages can cause electrode polarization, unwanted electrochemical reactions within the sample, and fouling of the electrodes.

SUMMARY

In general, this disclosure is related to a sensor, a system comprising a sensor, and a method for analyzing a fluid sample. In some examples, a sensor includes first and second operational amplifiers and an electrode array having first, second, third and fourth electrodes. In various embodiments, the electrodes can be mounted in a first face of a non-conductive housing of the sensor. Electrodes can be arranged linearly, and can be positioned such that the distance between each pair of adjacent electrodes is substantially the same. In some embodiments, the first electrode is coupled to the output of the first operational amplifier, the second electrode is coupled to the input of the first operational amplifier, and the third electrode is coupled to the inverting input of the second operational amplifier. The sensor can include a switch comprising a first and second position and coupled to the output of the second operational amplifier. In the first position, the switch couples the output of the second operational amplifier to the fourth electrode, and in the second position, the switch couples the output of the second operational amplifier to the third electrode. The switch can be positioned into the first or second position depending on the desired mode of operation of the sensor.

The sensor can include a sense resistor coupled between either the output of the first operational amplifier and the first electrode or between the output of the second operational amplifier and the switch. The sensor can include a differential amplifier configured to output an electrical signal corresponding to a current flowing through the sense resistor. For example, the differential amplifier can be configured to measure the voltage drop across the sense resistor while a current flows therethrough. The output of the differential amplifier in such a configuration corresponds to the current flowing through the sense resistor. Because of the location of the sense resistor (i.e., between the low-impedance outputs of the first and second operational amplifiers), current flow through the sample from the sensor will flow through the sense resistor, and therefore can be measured via the differential amplifier.

The sensor can be part of a system including a controller and an interface. One or both of the controller or interface can be integrated into the housing of the sensor. In some embodiments, a user can select a mode of operation of sensor via the interface. Selecting a mode of operation can include selecting a conductivity mode or an electrochemical mode. The switch may be placed in one of its first or second positions based on the selected mode of operation. In conductivity mode, an electrical potential can be applied across the sample via the electrode array. The conductivity of the sample causes a current to flow therethrough based on the applied potential. Thus, with a known applied potential and a measured resultant current, the conductivity of the sample, and in some embodiments, the combined concentration of ionized and soluble species, can be determined. The sensor can include switching means configured to direct current through the sample in a particular direction. Switching means can be switched at a particular frequency to provide a substantially AC potential to the sample, or can be set in a single direction to provide a DC potential to the sample. In electrochemical mode, the user can select a target constituent of the sample to analyze. An appropriate redox potential can be applied to the sample via the electrode array to initiate a redox reaction within the fluid sample. Current flow triggered by the redox reaction can be used to determine the concentration of the target constituent within the sample. Exemplary target constituents to be oxidized or reduced include peroxides, peracids and hypochlorite.

In either mode of operation, the controller can be configured to control the electrical potential applied to the sample, determine the current flowing through the sample, and determine the desired parameter from the determined current. Some additional parameters, such as the sample temperature, can have an effect on the relationship between the measured current and the desired sample parameters. As such, in some embodiments, additional sensors can be included in the housing of the sensor. For example, a temperature sensor can be disposed in one of the electrodes and placed in thermal contact with the sample via the electrode. The sensor can also include a lens for emitting light into and receiving light from the sample to perform additional analysis.

The details of one or more examples are set forth in the accompanying drawings and the description below. Other features, objects, and advantages will be apparent from the description and drawings, and from the claims.

DETAILED DESCRIPTION

Figure 1:
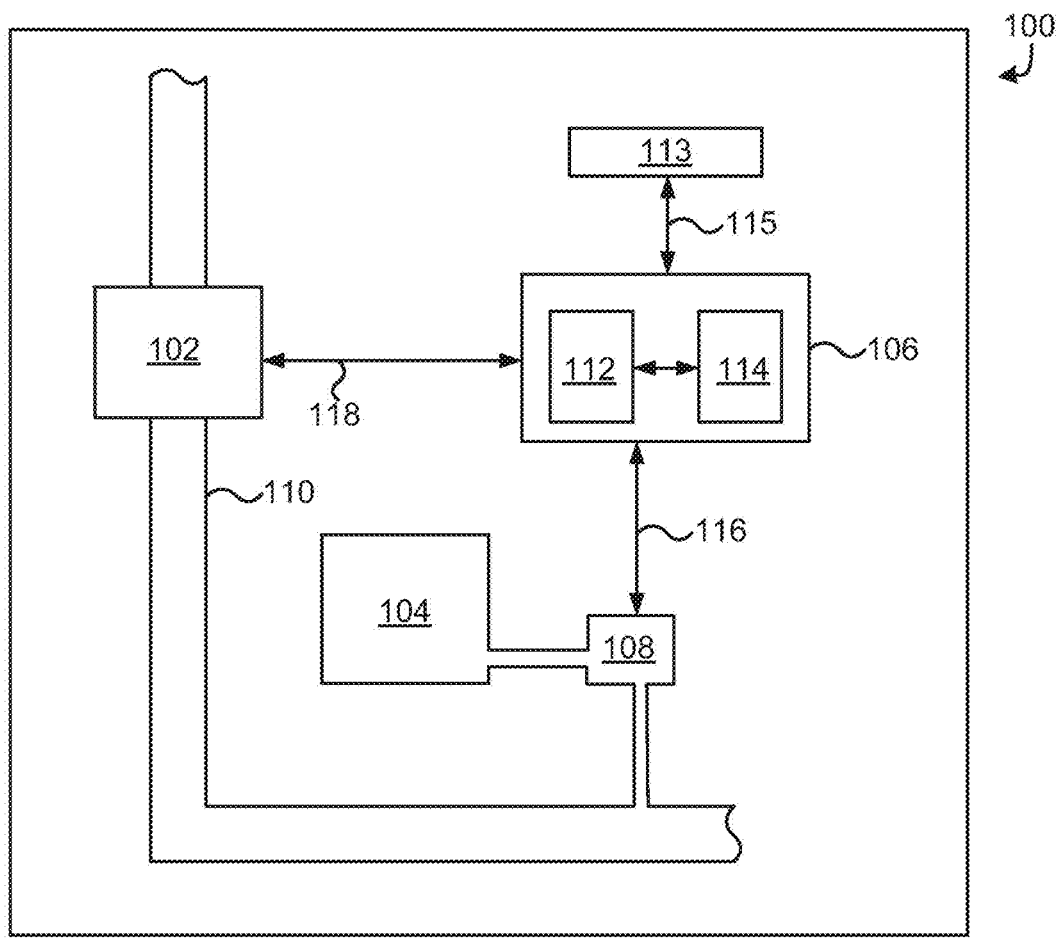
FIG. 1 is a diagram illustrating an example fluid system that may include a chemical sensor according to examples of the disclosure.

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Chemical sensors are used in a variety of applications in a variety of ways, including monitoring industrial processes. In some instances, a chemical sensor can be implemented as a portable, hand-held device that is used to periodically analyze, for example, the electrical characteristics of a fluid in an industrial process. Alternatively, a chemical sensor can be installed online to continuously analyze the electrical characteristics of a fluid in an industrial process. In either case, the chemical sensor may electrically analyze the fluid sample and determine different characteristics of the fluid, such as the concentration of one or more chemical species in the fluid.

As one example, chemical sensors can be used in industrial cleaning and sanitizing applications. During an industrial cleaning and sanitizing process, water is typically pumped through an industrial piping system to flush the piping system of product residing in pipes and any contamination build-up inside the pipes. The water may also contain a sanitizing agent that functions to sanitize and disinfect the piping system. The cleaning and sanitizing process can prepare the piping system to receive new product and/or a different product than was previously processed on the system.

A chemical sensor can be used to monitor the characteristics of flushing and/or sanitizing water flowing through a piping system during an industrial cleaning and sanitizing process. Either continuously or on an intermittent basis, samples of water are extracted from the piping system and delivered to the chemical sensor. At the chemical sensor, electrical current is directed into and received from the water sample and the received current and/or related parameters are used to evaluate the characteristics of the water sample. The chemical sensor may determine whether residual product in the piping system has been sufficiently flushed out of the pipes, for example, by determining that there is little or no residual product in the water sample. The chemical sensor may also determine the concentration of sanitizer in the water sample, for example, by measuring the electrical conductivity of the sample or by measuring an electrochemical response by the sanitizer in response to the electrical current emitted into the water sample. If it is determined that there is an insufficient amount of sanitizer in the water sample to properly sanitize the piping system, the amount of sanitizer is increased to ensure proper sanitizing of the system.

While such a chemical sensor for analyzing electrical characteristics of a fluid can have a variety of different configurations, in some examples, the chemical sensor is designed to have an electrode array via which electrical current is emitted into a fluid sample and also received from the fluid sample. Electrodes in the electrode array can comprise any electrically conductive material, but care should be taken to ensure that the electrode material does not react unfavorably with the fluid sample to be analyzed. The chemical sensor may include a housing that contains various electronic components of the sensor to interface with the electrode array and the sample. The housing can be designed to be readily installed through a variety of mechanical pipe and process fittings to electrically analyze a desired process fluid.

FIG. 1 is a conceptual diagram illustrating an example fluid system 100, which may be used to produce a chemical solution having electrical properties, such as a sanitizer solution exhibiting certain electrical conductivity and/or electrochemical properties. Fluid system 100 includes chemical sensor 102, a reservoir 104, a controller 106, and a pump 108. Reservoir 104 may store a concentrated chemical agent that can be blended with a diluent, such as water, to generate the chemical solution, or can be any other source for the sample to be characterized. Chemical sensor 102 is electrically coupled to fluid in fluid pathway 110 and can be configured to determine one or more characteristics of the solution traveling through the fluid pathway. Coupled, as used herein, can include being directly attached or adjoined by intervening elements.

The fluid pathway 110 can be a single fluid vessel or combination of vessels which carry a fluid sample through the fluid system 100 including, but not limited to, pipes, tanks, valves, pipe tees and junctions, and the like. In some instances, one or more components of the fluid pathway 110 can define an interface or opening sized to receive or otherwise engage with the chemical sensor 102. In operation, chemical sensor 102 can communicate with controller 106, and controller 106 can control fluid system 100 based on the fluid characteristic information generated by the chemical sensor.

Controller 106 is communicatively connected to chemical sensor 102 and pump 108. Controller 106 includes processor 112 and memory 114. Controller 106 communicates with pump 108 via a connection 116. Signals generated by chemical sensor 102 are communicated to controller 106 via a wired or wireless connection, which in the example of FIG. 1 is illustrated as wired connection 118. Memory 109 stores software for running controller 106 and may also store data generated or received by processor 112, e.g., from chemical sensor 102. Processor 112 runs software stored in memory 114 to manage the operation of fluid system 100.

As described in greater detail below, chemical sensor 102 is configured to analyze electrical properties of a sample of fluid flowing through fluid pathway 110. Chemical sensor 102 may include an electrode array configured to interface with the fluid sample and to provide electrical current thereto and receive electrical current therefrom. The sensor 102 can include electrical components configured to receive feedback signals from the fluid sample to govern electrical operation of the sensor 102.

Independent of the specific composition of the fluid generated by fluid system 100, the system can generate fluid in any suitable fashion. Under the control of controller 106, pump 108 can mechanically pump a defined quantity of concentrated chemical agent out of reservoir 104 and combine the chemical agent with water to generate a liquid solution suitable for the intended application. Fluid pathway 110 can then convey the liquid solution to an intended discharge location. In some examples, fluid system 100 may generate a flow of liquid solution continuously for a period of time such as, e.g., a period of greater than 5 minutes, a period of greater than 30 minutes, or even a period of greater than 24 hours. Fluid system 100 may generate solution continuously in that the flow of solution passing through fluid pathway 110 may be substantially or entirely uninterrupted over the period of time.

In some examples, monitoring the characteristics of the fluid flowing through fluid pathway 110 can help ensure that the fluid is appropriately formulated for an intended downstream application. Monitoring the characteristics of the fluid flowing through fluid pathway 110 can also provide feedback information, e.g., for adjusting parameters used to generate new fluid solution. For these and other reasons, fluid system 100 can include a sensor to determine various characteristics of the fluid generated by the system. The sensor can engage directly with the fluid pathway 110 to monitor fluid characteristics, or can alternatively receive fluid from the fluid system 100 separately from the fluid pathway 110.

In the example of FIG. 1, fluid system 100 includes chemical sensor 102. The chemical sensor 102 can engage the fluid pathway 110 in any number of ways, such as interfacing with a tee configuration in a pipe in the fluid pathway 110, being inserted into a port of a tank or other fluid vessel through which fluid periodically flows, or the like. Chemical sensor 102 may utilize components thereof to determine one or more characteristics of the fluid flowing through fluid pathway 110. Example characteristics include, but are not limited to, the concentration of one or more chemical compounds within the fluid (e.g., the concentration of one or more active agents added from reservoir 104 and/or the concentration of one or more materials being flushed from piping in fluid system 100), the temperature of the fluid, optical properties such as the fluorescence and/or turbidity of the fluid, the electrical conductivity of the fluid, the pH of the fluid, the flow rate at which the fluid moves through past the chemical sensor, and/or other characteristics of the fluid that may help ensure the system from which the fluid sample being analyzed is operating properly. Chemical sensor 102 may communicate detected characteristic information to controller 106 via connection 118.

Chemical sensor 102 may be controlled by controller 106 or one or more other controllers within fluid system 100. For example, chemical sensor 102 may include a device controller (not illustrated in FIG. 1) that controls the chemical sensor to direct electrical current into the fluid under analysis and also to receive electrical current back from the fluid using the electrode array. The device controller may be positioned physically adjacent to the other components of the chemical sensor, such as inside a housing that houses electrical components of the chemical sensor. In such examples, controller 106 may function as a system controller that is communicatively coupled to the device controller of chemical sensor 102. The system controller 106 may control fluid system 100 based on electrical characteristic data received from and/or generated by the device controller. In other examples, chemical sensor 102 does not include a separate device controller but instead is controlled by controller 106 that also controls fluid system 100. Therefore, although chemical sensor 102 is generally described as being controlled by controller 106, it should be appreciated that fluid system 100 may include one or more controllers (e.g., two, three, or more), working alone or in combination, to perform the functions attributed to chemical sensor 102 and controller 106 in this disclosure. Devices described as controllers may include processors, such as microprocessors, digital signal processors (DSPs), application specific integrated circuits (ASICs), field programmable gate arrays (FPGAs), or any other equivalent integrated or discrete logic circuitry, as well as any combinations of such components.

In the example illustrated in FIG. 1, processor 112 of controller 106 can receive determined electrical characteristic information from chemical sensor 102 and compare the determined characteristic information to one or more thresholds stored in memory 114, such as one or more concentration thresholds. Based on the comparison, controller 106 may adjust fluid system 100, e.g., so that the detected characteristic matches a target value for the characteristic. In some examples, controller 106 starts and/or stops pump 108 or increases and/or decreases the rate of pump 108 to adjust the concentration of a chemical compound flowing through fluid pathway 110. Starting pump 108 or increasing the operating rate of pump 108 can increase the concentration of the chemical compound in the fluid. Stopping pump 108 or decreasing the operating rate of pump 108 can decrease the concentration of chemical compound in the fluid. In some additional examples, controller 106 may control the flow of water that mixes with a chemical compound in reservoir 104 based on determined characteristic information, for example, by starting or stopping a pump that controls the flow of water or by increasing or decreasing the rate at which the pump operates. Although not illustrated in the example fluid system 100 of FIG. 1, controller 106 may also be communicatively coupled to a heat exchanger, heater, and/or cooler to adjust the temperature of fluid flowing through fluid pathway 110 based on characteristic information received from chemical sensor 102.

In yet other examples, chemical sensor 102 may be used to determine one or more characteristics of a stationary volume of fluid that does not flow through a flow chamber of the fluid system. For example, chemical sensor 102 may be implemented as an offline monitoring tool (e.g., as a handheld sensor), that requires filling a separate vessel with a fluid sample manually extracted from fluid system 100. The separate vessel can, in some embodiments, be integrated into the chemical sensor. Alternatively, the chemical sensor 102 can engage a portion of the fluid system 100 configured to receive and hold a stationary volume of the fluid, such as a stop-flow device, or an otherwise external vessel for receiving fluid and engaging the chemical sensor 102. In some embodiments, a controller 106 can control a system of pumps and/or valves to direct a finite amount of the sample to be measured into such a stationary vessel outfitted with a sensor 102.

Fluid system 100 in the example of FIG. 1 also includes reservoir 104, pump 108, and fluid pathway 110. Reservoir 104 may be any type of container that stores a chemical agent for subsequent delivery including, e.g., a tank, a tote, a bottle, and a box. Reservoir 104 may store a liquid, a solid (e.g., powder), and/or a gas. Pump 108 may be any form of pumping mechanism that supplies fluid from reservoir 104. For example, pump 108 may comprise a peristaltic pump or other form of continuous pump, a positive-displacement pump, or any other type of pump appropriate for the particular application. In examples in which reservoir 104 stores a solid and/or a gas, pump 108 may be replaced with a different type of metering device configured to deliver the gas and/or solid chemical agent to an intended discharge location. Fluid pathway 110 in fluid system 100 may be any type of flexible or inflexible tubing, piping, or conduit.

Figure 2:
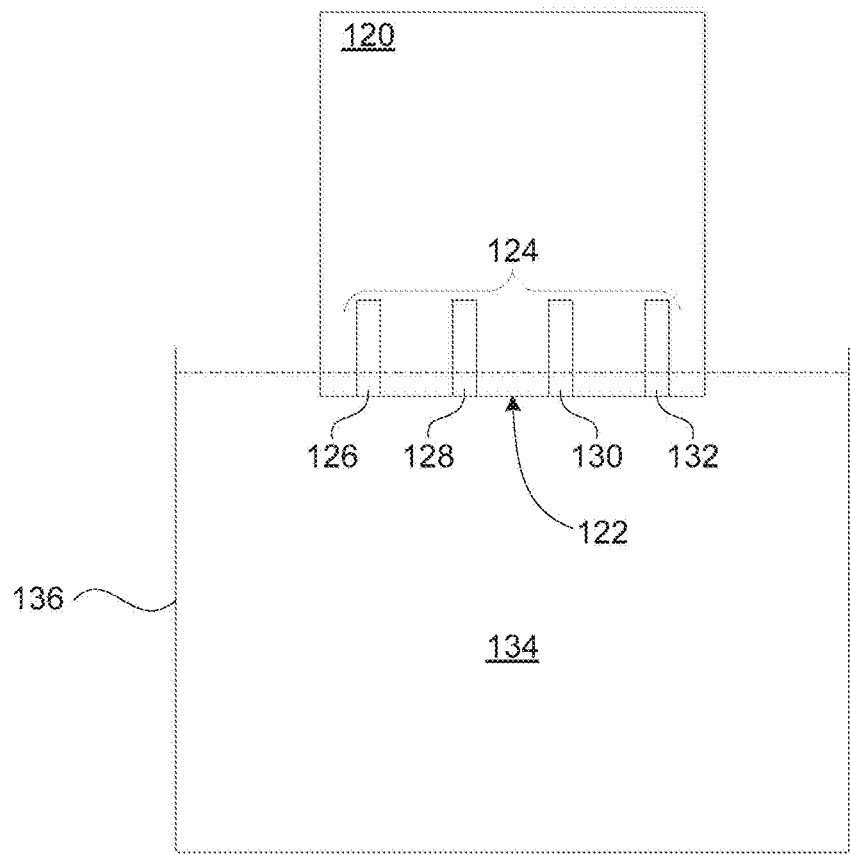
FIG. 2 is a view of an exemplary chemical sensor disposed in a fluid sample.

In the example of FIG. 1, chemical sensor 102 determines a characteristic of the fluid flowing through fluid pathway 110 (e.g., concentration of a chemical compound, conductivity, temperature or the like) and controller 106 controls fluid system 100 based on the determined characteristic and, e.g., a target characteristic stored in memory 114. FIG. 2 is a view of an exemplary chemical sensor disposed in a fluid sample. FIG. 2 shows at least a portion of sensor 102 having a housing 120 and an electrode array 124. Housing 120 can be made from any appropriate non-conductive material, such as a rubber, plastic, ceramic or the like. The electrode array 124 in FIG. 2 comprises a first 126, second 128, third 130, and fourth 132 electrode, each electrically coupled to the fluid sample 134. Fluid sample 134 is shown as being contained in analysis chamber 136. Analysis chamber 136 can be any type of fluid container and can be inline or isolated from a fluid system. For example, analysis chamber 136 can represent a tee in a pipe through which a fluid under analysis flows or any part of the fluid pathway 110. Alternatively, analysis chamber 136 can represent an isolated volume of such a sample automatically or manually extracted from the fluid system 100.

Electrode array 124 is shown comprising four electrodes. Electrodes 126-132 can comprise any electrically conductive material. Exemplary electrodes 126-132 can comprise conductive materials that are nonreactive to the fluid sample 134, such as gold, platinum, stainless steel or other nonreactive metals or alloys, or carbon-based materials such as boron-doped diamond, glassy carbon or graphite. Some electrodes can be designed for use with a specific fluid sample. In some embodiments, electrodes 126-132 are arranged linearly, such that the second electrode 128 is positioned along the line between the first 126 and fourth 132 electrodes, and the third electrode 130 is positioned along the line between the second 128 and fourth 132 electrodes. In further embodiments, the spacing between each adjacent electrode is equal. That is, the distance between the first 126 and second 128 electrodes is the same as the distance between the second 128 and third 130 electrodes, and between the third 130 and fourth 132 electrodes.

In general, electrodes 126-132 provide electrical current to and receive electrical signals and current from the fluid sample 134. Accordingly, during operation, electrodes 126-132 are placed in electrical communication with the fluid sample. Electrical current provided by the chemical sensor 102 can include either direct or alternating currents produced by applying voltages to the electrodes. In some configurations, providing a voltage to the sample from a particular electrode can result in current being provided to the sample via the same electrode. Accordingly, in some configurations, providing a current to the sample and providing an electrical potential to the sample are equivalent. In some systems, the nature of the fluid sample and the magnitude of an applied voltage determine the relationship between the applied voltage and resulting current, for example.

Figure 3:
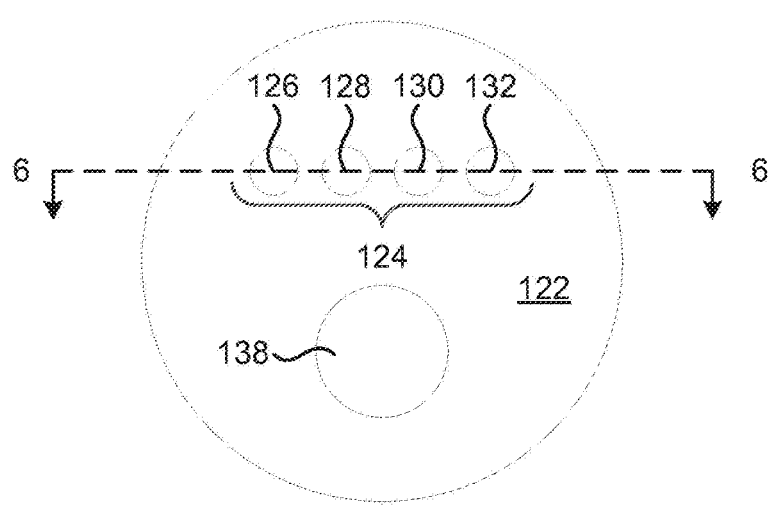
FIG. 3 is an illustrative example of a first face of a housing comprising an electrode array.

In some embodiments, the housing 120 of the sensor 102 is non-conductive so that electrodes 126-132 disposed therein are substantially electrically isolated from one another within the sensor 102. The housing 120 can include a first face 122 in which the electrode array 124 can be mounted. Electrodes 126-132 can be mounted in the first face 122 such that the surface of each electrode is flush with the first face 122. FIG. 3 is an illustrative example of a first face of a housing comprising an electrode array. Electrode array 124 is disposed in the first face 122 of a housing, and comprises first 126, second 128, third 130 and fourth 132 electrodes. Electrodes 126-132 are substantially equally spaced along a linear arrangement. During operation, first face 122 can be submerged in a fluid sample, enabling electrical contact between electrodes 126-132 and the fluid sample. In some embodiments, the first face 122 can include additional components, enabling additional measurements by the sensor 102. For example, such as is shown in FIG. 3, the first face 122 can include a lens 138 for coupling light between the interior or the sensor 102 and the fluid sample. Lens 138 can be configured to emit light from the sensor 102 into the fluid sample, or receive light from the sample and direct it back into the housing of the sensor 102. In some embodiments, received light can be scattered or fluoresced by the sample in response to light directed to the sample via lens 138.

Figure 4A:
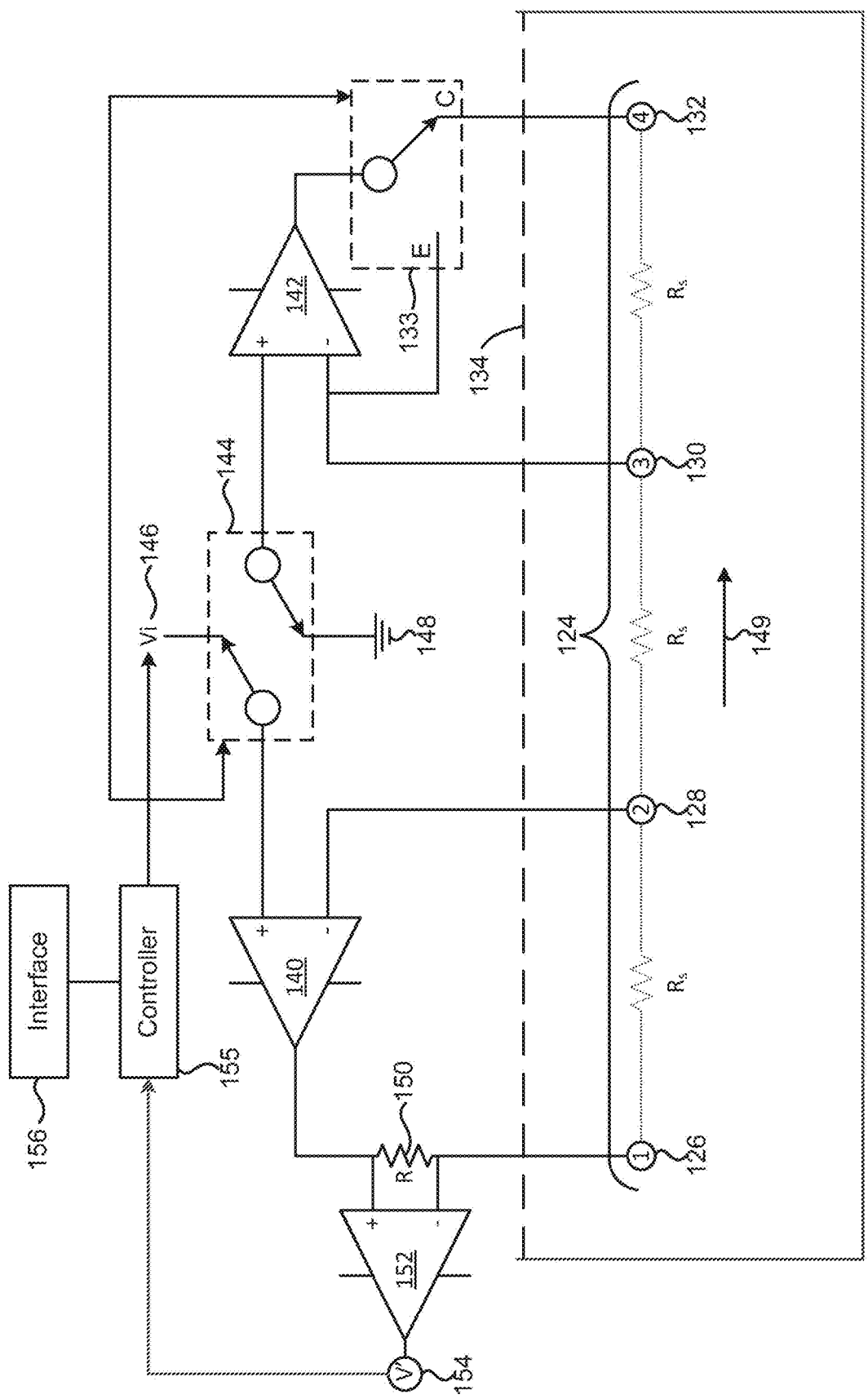
FIGS. 4A and 4B are a schematic circuit diagrams showing exemplary circuitry for controlling the chemical sensor.

The housing 120 of the sensor 102 can further include circuitry for controlling the electrical signals sent to the fluid sample via the electrode array 124. FIG. 4A is a schematic circuit diagram showing exemplary circuitry for controlling the chemical sensor. The circuitry of FIG. 4A includes first 140 and second 142 operational amplifiers, each having inverting and non-inverting inputs and an output. In some embodiments, the non-inverting input of each operational amplifier is coupled to a switching mechanism 144, which effectively couples one of the non-inverting inputs to a voltage source 146 and the other non-inverting input to voltage source 148. In the illustrated embodiment, voltage source 146 is shown as having a voltage value of Vi, while voltage source 148 is shown as being 0V (ground).

It will be appreciated that these values are exemplary and are shown as such for the purposes of describing aspects of the operation of the invention. In general, voltage sources 146 and 148 can output any arbitrary voltages that provide an appropriate voltage difference therebetween. As such, in some embodiments, the operational amplifier receiving a voltage at its non-inverting input from voltage source 146 is defined as the powered amplifier, while the operational amplifier receiving a voltage at its non-inverting input from voltage source 148 is defined as the reference amplifier. These terms are not limiting, but rather are intended to illustrate that one (powered) amplifier can receive a voltage that is some defined amount above or below a reference voltage applied to the other (reference) amplifier. "Vi" and "ground," are used in the illustrated embodiments and throughout the description merely to indicate a voltage difference of Vi, and should not be seen as limiting.

Switching mechanism 144 and the voltage source 146 can be controlled by a controller 155. While shown as controlled by a single controller 155, switching mechanism 144 and voltage source 146 can be controlled by separate controllers. In some embodiments, controller 155 can include, be included in, or otherwise communicate with system controller 106 shown in FIG. 1. In the illustrated embodiment of FIG. 4A, switching mechanism couples the non-inverting input of the first operational amplifier 140 to the voltage source 146 at voltage Vi and the non-inverting input of the second operational amplifier 142 to ground 148. The switching mechanism can switch which non-inverting input is coupled to the voltage source 146 and which is coupled to ground 148 at a predetermined frequency, effectively producing AC square waves at each non-inverting input, 180 degrees out of phase with one another.

The diagram of FIG. 4A shows an exemplary arrangement of the electrodes in the electrode array 124. As shown, the first electrode 126 is coupled to the output of the first operational amplifier 140 and the second electrode 128 is coupled to the inverting input of the first operational amplifier 140. The output of the second operational amplifier 142 can be coupled to the input of a switch 133 with outputs coupled to the third 130 (position E) and fourth 132 (position C) electrodes. In some embodiments, the switch 133 can be in communication with controller 155. The third electrode 130 can be additionally coupled to the inverting input of the second operational amplifier 142. In the configuration of FIG. 4A, switch 133 is in position C, connected to output to the fourth electrode 132, and each electrode 126-132 is shown as being disposed in a fluid sample 134.

The fluid sample 134 has associated with it an electrical conductivity. Accordingly, a distance between two points has associated with it an electrical resistance. In the illustrated embodiment, electrodes 126-132 are evenly spaced apart, and so the electrical resistance between each pair of adjacent electrodes is generally equal. The resistance of the fluid sample 134 between adjacent electrodes is shown schematically by a resistor illustrated in dotted lines and labeled Rs. It will be appreciated that alternative configurations are possible in which the electrodes need not be spaced equally apart. Linearly arranged electrodes of a known spacing can be used and, since the resistance between electrodes is proportional to the distance between them, relationships between unequal resistances can be determined from the known spacing of electrodes.

An arrangement such as that shown in FIG. 4A can be used, for example, to determine the electrical conductivity of a fluid sample. In an exemplary operation, the non-inverting input of the first operational amplifier 140 is coupled to voltage source 146 and held at voltage Vi while the non-inverting input of the second operational amplifier 142 is coupled to ground. First operational amplifier 140 will operate such that it will output an electrical signal in an attempt to produce voltage Vi at the inverting input of the amplifier 140, coupled to the second electrode 128. Similarly, the second operational amplifier 142 will operate to hold the inverting input of the amplifier 142, which is coupled to the third electrode 130, at ground. Accordingly, the first 140 and second 142 operational amplifiers will act to produce a voltage differential of Vi between the second 128 and third 130 electrodes. In the illustrated embodiment, the resistance between these electrodes is shown as Rs. By Ohm's law, a voltage drop Vi over resistance Rs suggests a current of I=Vi/Rs is flowing through the solution between the second 128 and third 130 electrodes in the direction of arrow 149. Because operational amplifiers tend to have very high input impedances, this current is not produced by the inverting inputs coupled to the second 128 and third 130 electrodes. Rather, the first 140 and second 142 operational amplifiers output an appropriate signal to create such a current.

Since current flows through the system in the direction of arrow 149, and cannot flow into or out of inputs of the operational amplifiers (i.e., second 128 and third 130 electrodes), current must flow through the system from the output of the first operational amplifier 140, acting as a current source, to the output of the second amplifier 142, acting as a current sink. Analogously, current flows into the fluid sample 134 via the first electrode 126, through the fluid sample 134, and out of the fluid sample 134 via the fourth electrode 132. In some embodiments, a sense resistor 150 of a known resistance R is disposed between the output of the first operational amplifier 140 and the first electrode 126. In some exemplary embodiments, R is 33Ω. The voltage drop across the sense resistor 150 can be measured by means known in the art. In the illustrated embodiment, a differential amplifier 152 is positioned with inputs on either side of the sense resistor 150. Differential amplifier 152 is arranged to provide an output corresponding to the difference in voltage received at its input signals. In this configuration, the difference in input signals will be the voltage drop across sense resistor 150. The output V' of differential amplifier 152 can be measured by a meter 154. In some embodiments, the output of a meter 154 or differential amplifier 152 can be communicated to controller 155.

From the measurement of the output voltage V' of the differential amplifier 152, the voltage drop V across the sense resistor 150 can be determined from known amplifier parameters. Combined with the known resistance R of the sense resistor 150, the current flowing through the sense resistor 150 can be determined: I=V/R. Because current is flowing in a single loop in the system (from first operational amplifier 140 through sense resistor 150 to the first electrode 126, from the first electrode 126 into the fluid sample 134, through the fluid sample 134 to the fourth electrode 132, and from the fourth electrode 132 through switch 133 to the second operational amplifier 142), the current through the sense resistor 150 is substantially the same as the current through the fluid sample 134. That is: V/R=I=Vi/Rs; or V/R=Vi/Rs. Because Vi is a known applied voltage, R is a known resistance, and the voltage drop V across the sense resistor 150 can be determined from the measurement of V' from the differential amplifier 152, Rs can be solved for: Rs=R×Vi/V. The resistance Rs of the fluid sample 134 can be used in conjunction with known dimensions of the electrode array 124 in order to calculate the conductivity of the fluid sample 134. In some embodiments, controller 155 can determine sample conductivity using the output of the meter 154. In one example, controller 155 can utilize preprogrammed dimensions of the electrode array 124 along with a known applied potential Vi from voltage source 146 to calculate the sample conductivity. In a second example, controller 155 can determine the conductivity of the sample from a lookup table stored in memory. Lookup table can, in some examples, be generated by running conductivity calibration standards.

During conductivity measurements, the difference between voltage sources 146 and 148, represented as Vi, is kept generally low so as to not induce electrochemical corrosion that can damage the electrodes. Larger voltages can cause electrochemical reactions in the fluid sample 134 that can be damaging to the electrodes or alter the fluid sample 134 itself. In some embodiments, Vi is between 0.1 and 0.3 volts, and in further embodiments, Vi can be adjustable on the fly from a low to a higher voltage. In such cases, Vi can be adjusted in response to the conductivity range of the sample 134. For example, a more conductive sample (i.e., a sample having a lower resistance Rs) can be analyzed with a lower value of Vi than can a less conductive sample. In addition, switching mechanism 144 can act to alternate the direction of current flow in the sample 134. When the non-inverting input of the second operational amplifier 142 is tied to the voltage source 146, current will flow in the opposite direction when compared to the configuration in which the non-inverting input of the first operational amplifier 140 is tied to the voltage source 146. Switching mechanism 144 can alternate which non-inverting input is tied to the voltage source 146 while tying the other non-inverting input to ground. That is, switching mechanism 144 can cycle the non-inverting input of each operational amplifier between Vi and ground 180 degrees out of phase with one another. In some embodiments, switching is performed at a sufficiently high rate to avoid electrode polarization and potentially resulting measurement errors. In some embodiments, switching is performed at a frequency of at least 1 kHz. Switching mechanism 144 can comprise, for example, solid state switches controlled by a controller 155.

Figure 5A:
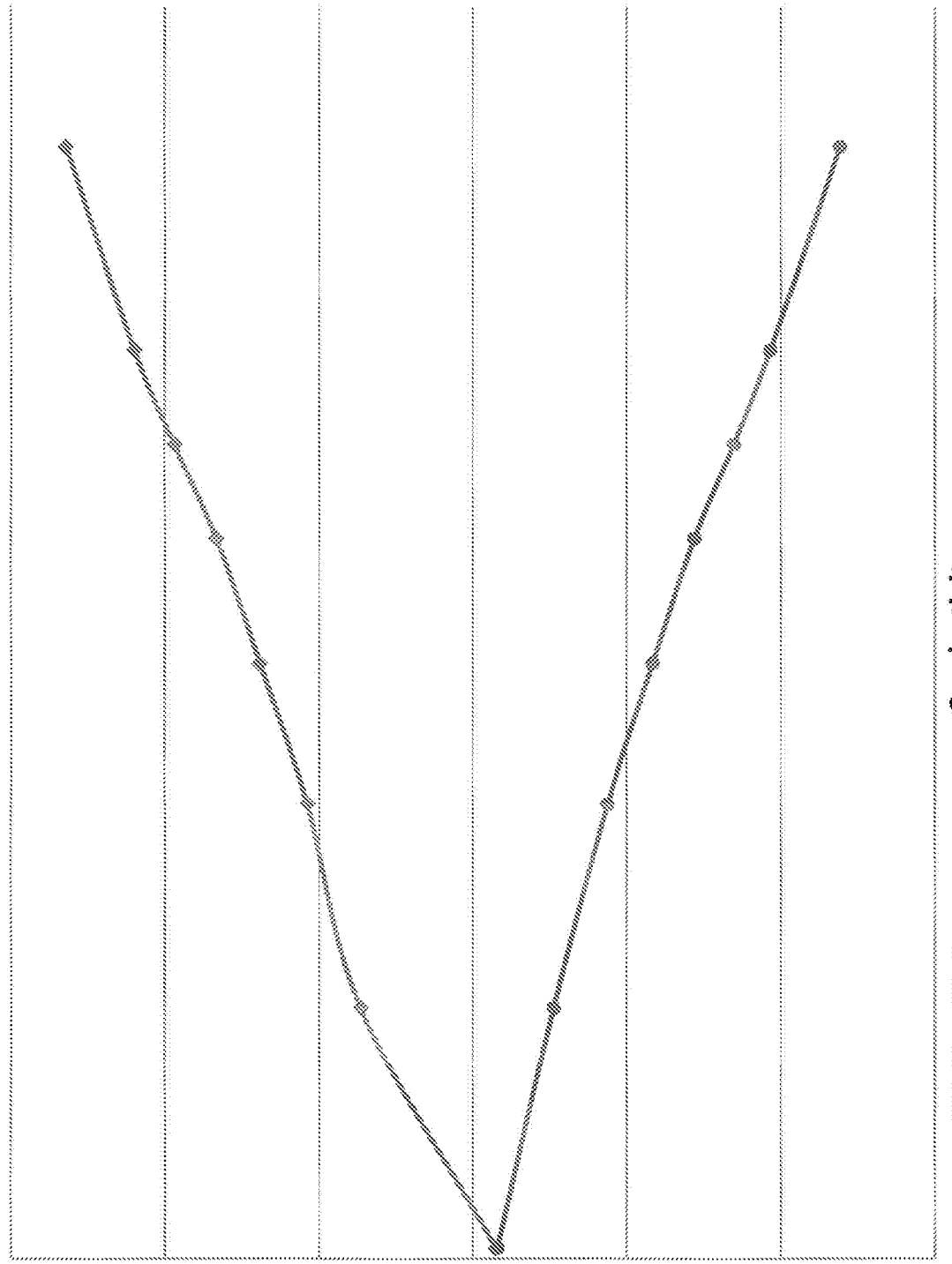
FIGS. 5A-5D are exemplary plots illustrating measurements using the circuit of FIGS. 4A and 4B.

During operation, switching mechanism 144 can cause an alternating current to flow through sense resistor 150. Accordingly, the voltage drop across the sense resistor 150 will change sign as the current changes direction. In some embodiments, differential amplifier 152 comprises a built-in offset, such that the output of the amplifier 152 will be above or below the offset value depending on the sign of the sensed voltage drop. In some such embodiments, the voltage V' from the differential amplifier 152 will always be positive, regardless of the direction of current flow through the sense resistor 150—a voltage drop in one direction will result in an output voltage of a certain value above the offset, while a voltage drop in the other direction will result in an output voltage of a value below the offset. Exemplary data is illustrated in the plot of FIG. 5A, which shows the voltage drop across the sense resistor R in both directions with relation to the offset as conductivity of the sample is increased.

In embodiments in which an alternating current voltage is applied from the voltage source 146 and the differential amplifier 152 comprises a built-in offset, the output voltage V' from the differential amplifier 152 can alternate on either side of the offset voltage. Accordingly, for a given conductivity, the controller 155 will receive two different output voltage signals depending on the direction of current flow. In some such embodiments, the controller can calculate the difference between the two output voltage signals and use the calculated difference to determine the conductivity of the fluid sample. In using the difference measurement, both polarities of circuit operation are used. This can average out slight variations due to inhomogeneity in sample flow or turbulence past the sensor. In addition, the difference measurement yields a larger measured voltage for greater precision.

Figure 5B:
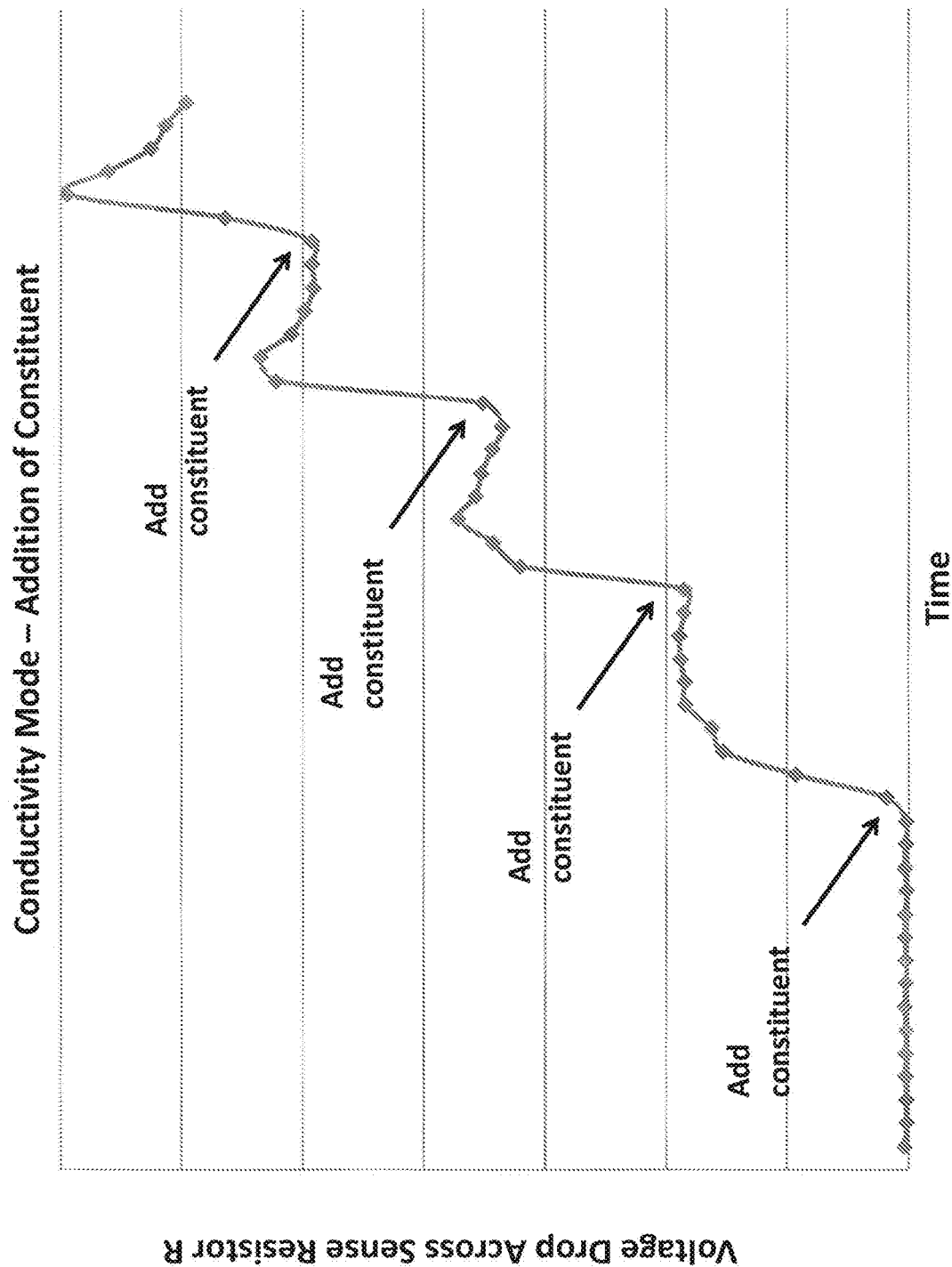

Measurements of the conductivity of a sample can provide information indicative of a combined concentration of ionized and soluble species in a fluid sample, such as sanitizers, detergents, acids, and bases in an aqueous solution, for example. FIG. 5B is an exemplary plot illustrating the change in the voltage drop across the sense resistor 150, and thus the conductivity, with the addition of a conductive constituent such as hypochlorite, peracid, or caustic. In some embodiments, the controller can determine the sample conductivity and subsequently determine the sample concentration via a lookup table stored in memory, for example. As discussed elsewhere herein, when determining electrical conductivity according to methods herein described, the voltage applied to the sample is kept relatively low in order to prevent unwanted electrochemical reactions from taking place. However, in some situations, such electrochemical reactions can be utilized to provide additional information about the sample.

In some configurations, fluid sample 134 comprises constituents that are electrochemically active. When a sufficient potential is applied to such a fluid sample, reduction and/or oxidation reactions can occur. In general, a sufficiently high potential for causing electrochemical reactions is such that it creates energetically favorable conditions for electrons to transfer (i) from the solution to an electrode or (ii) from an electrode to the solution. The applied potential necessary to cause the transfer of charge between an electrode and a particular constituent in the fluid sample (the redox potential), depends on the constituent gaining or losing the electrons. In some examples, electrochemically induced redox reactions can be used to selectively measure peroxides, peracids, and/or hypochlorite. In some embodiments, the redox potential for a target constituent is between approximately −0.8V and −1.0V. In some fluid systems, then, a target constituent with a known redox potential can be driven to electrochemical reaction to determine the concentration of the constituent in the fluid sample.

Such reactions can cause a transfer of charge between the electrodes and the fluid sample and result in a current flow. For example, two common cleaning products are hydrogen peroxide and chlorine (bleach). For acidic peroxide, the electrochemical reduction equation is $H_2O_2 + 2H^+ + 2e^- \rightarrow 2H_2O$. Hydrogen peroxide is reduced to water. For alkaline bleach, electrochemical reduction is $OCl^- + H_2O + 2e^- \rightarrow Cl^- + 2OH^-$. Here hypochlorite is reduced to chloride. Each of these processes will conduct a flow of current in the sensor when the voltage differential is −0.8V.

Figure 4B:
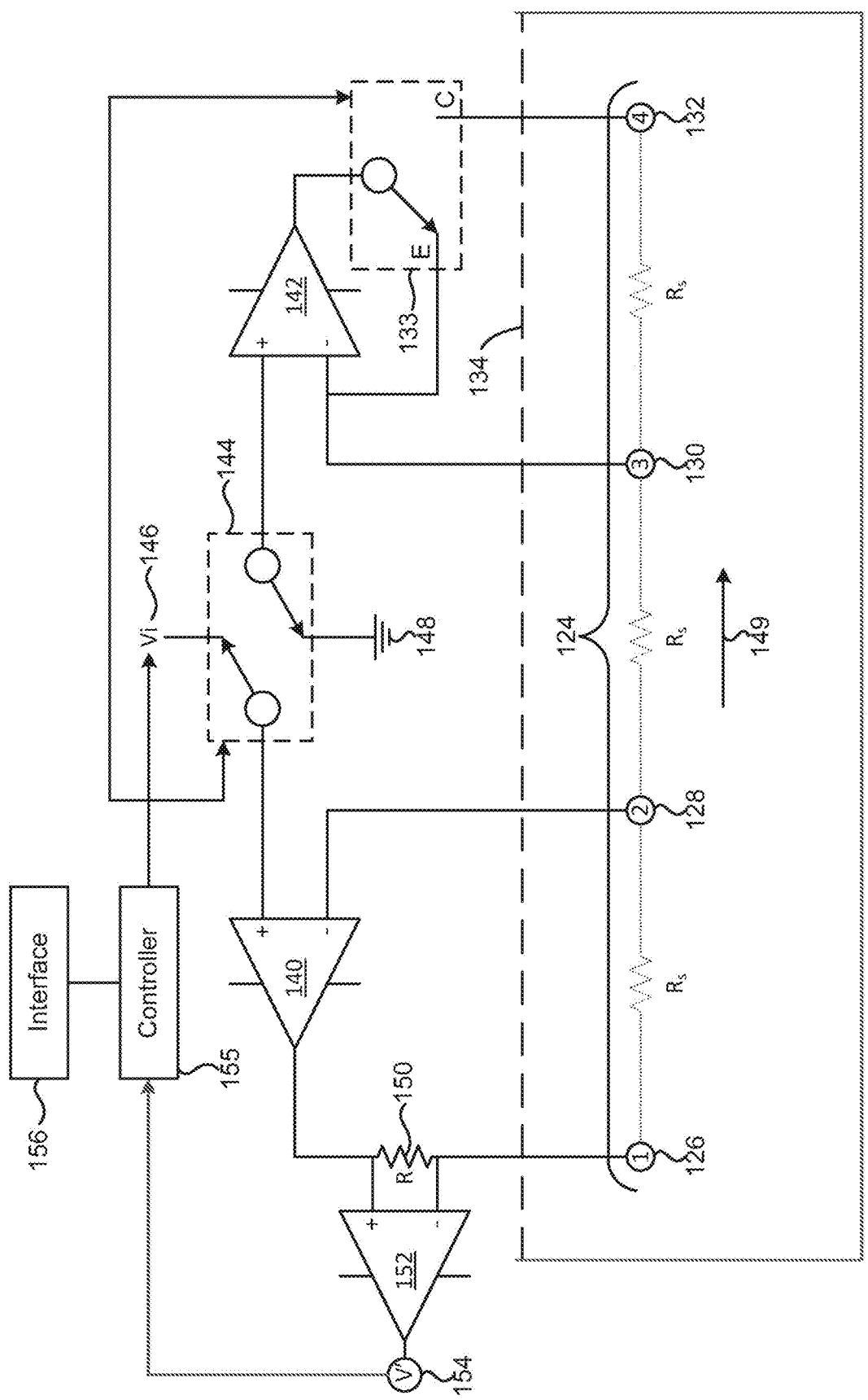

During exemplary operation utilizing an electrochemical reaction, switch 133 can be set to position E as shown in FIG. 4B, coupling the output of the second operational amplifier 142 to the third electrode 130. In such a configuration, the fourth electrode 132 can be used for a separate measurement or can otherwise be left unused. The electrode array 124 of the sensor can be disposed in a fluid sample 134 having a target constituent with a known redox potential Vr. Once the electrode array 124 is disposed in the sample, voltage source 146 is set by controller 106 to output Vi=Vr and voltage source 148 is set to 0V (that is, voltage source 148 represents ground). Thus, the non-inverting input of the first operational amplifier 140 is held at a voltage Vi=Vr by a voltage source 146 and the non-inverting input of the second operational amplifier 142 is tied to ground 148.

Alternatively, voltage sources 146 and 148 can be held at any voltages such the difference therebetween is a redox potential. That is, the voltage source 146 can define and be coupled to the non-inverting input of the powered amplifier, while voltage source 148 can define and be coupled to the non-inverting input of the reference amplifier. For the case of alkaline bleach, for example, Vi (or the difference in voltages applied to the non-inverting inputs of operational amplifiers 140 and 142) can be set to −0.8V.

During exemplary operation, a known redox potential of a target constituent can be applied between the non-inverting inputs of the first 140 and second 142 operational amplifiers. The operational amplifiers 140 and 142 will act so that the redox potential will be present between second 128 and third 130 electrodes. In embodiments in which electrodes 126-132 are arranged linearly and are equally spaced, then as discussed elsewhere herein, the redox potential will be present between the first 126 and second 128 electrodes.

As the redox potential is applied across various electrodes disposed in the fluid sample 134, if it is energetically favorable for the target constituent of the fluid sample 134 to lose electrons (oxidation) or gain electrons (reduction), then target constituent molecules proximate the third electrode 130 can either give electrons to or gain electrons from the third electrode via the output of the second operational amplifier 142. In some embodiments, redox reactions can occur proximate the first electrode 126, with electrons being lost or gained therefrom via the output of the first operational amplifier 140. Because the second electrode 128 is coupled to the high-impedance inverting input of the first operational amplifier 140, constituents of the fluid sample 134 cannot lose electrons to or gain electrons from the second electrode 128. However, because the first electrode 126 is coupled to the output of the first operational amplifier 140 and third electrode 130 is coupled to the output of the second operational amplifier 142 via switch 133, electrons can be transferred between first 126 and third 130 electrodes and the fluid sample 134.

For example, in an exemplary reduction reaction, a target constituent molecule proximate the third electrode 130 gains an electron from the third electrode 130 (by way of the low impedance output of the second operational amplifier 142 and switch 133). In order to maintain appropriate potentials and to complete the circuit, the first operational amplifier 140 can inject current into the fluid sample 134 via its output and the first electrode 126. That is, electrons will be emitted into the fluid sample 134 via reduction of a target constituent at the third electrode 130 and will be extracted via the first electrode 126. This flow of electrons creates a current path flowing from the output of the first operational amplifier 140 to the first electrode 126, through the fluid sample 134, and to the output of the second operational amplifier 142 via third electrode 130 and switch 133.

Thus, in oxidation or reduction reactions, the transfer of charge due to the electrical potentials maintained in the fluid sample and the resultant electrochemical reactions can create an electrochemical current flowing through the fluid sample 134 from the first electrode 126 to the third electrode 130 (i.e. from the output of the first operational amplifier 140 to the output of the second operational amplifier 142). In some embodiments, as charge is depleted/acquired on first 126 and/or third 130 electrodes, the second electrode 128 can provide feedback from the fluid sample 134 to first 140 operational amplifier, which acts to source and sink current to maintain desired voltages throughout the system, such as, in some exemplary embodiments, the redox potential between the second 128 and third electrodes 130. In some embodiments, at a steady state, first operational amplifier 140 provides current through the first electrode 126 to the sample 134, through the sample 134 to the third electrode 130, and from the third electrode 130 to the output of the second operational amplifier 142 via switch 133. In other embodiments, current can flow in the opposite direction through the fluid sample 134.

Figure 5C:
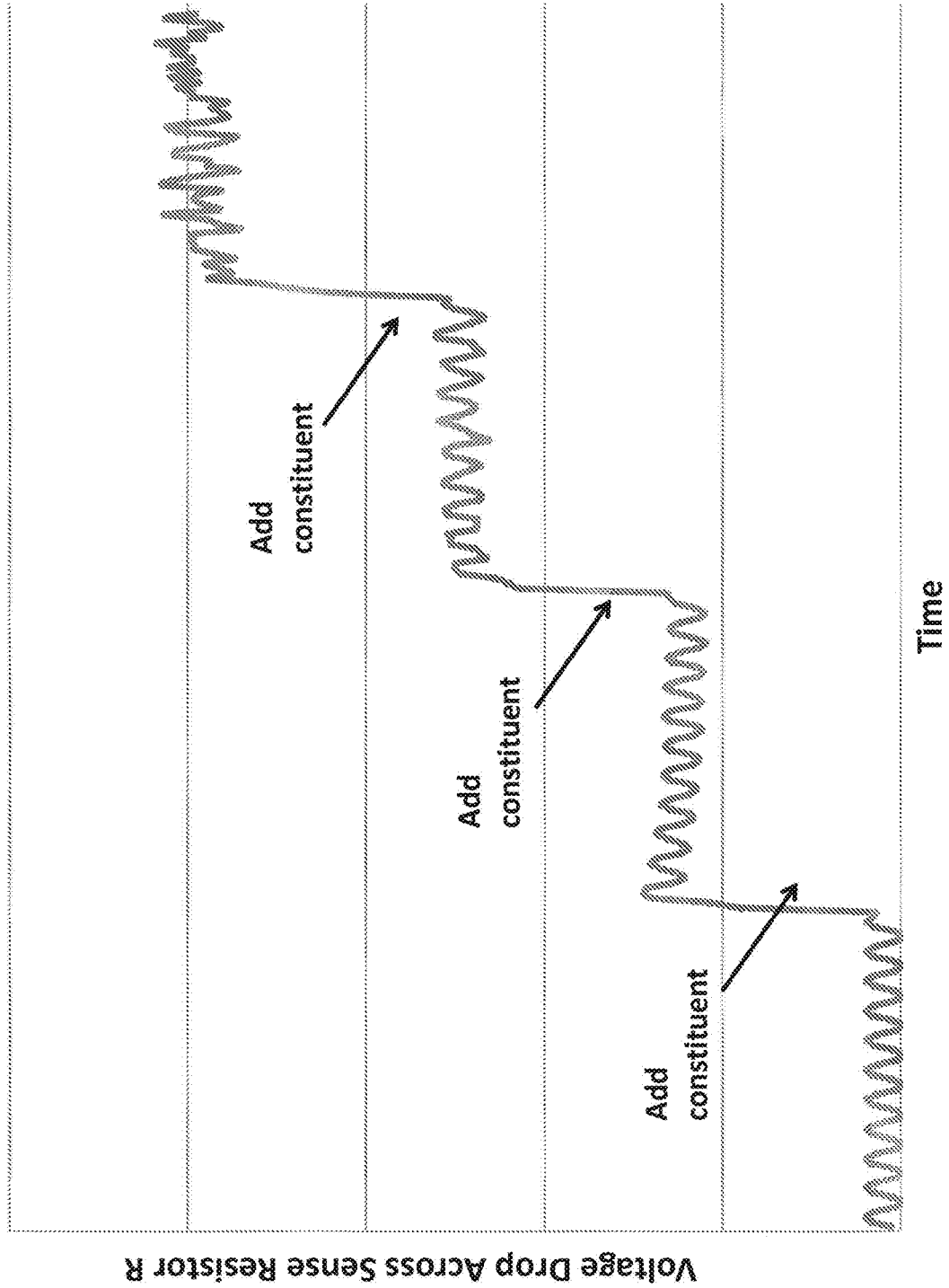

Because the electrochemical current results from the electrochemical oxidation or reduction of a target constituent, the magnitude of the electrochemical current is related to the concentration of the target constituent proximate the electrodes. Accordingly, in some embodiments, a sense resistor 150 is disposed between the output of the first operational amplifier 140 and the first electrode 126, for example. As described elsewhere herein, the current flowing through the sense resistor 150 can be measured as a voltage drop from which the current flowing through the sample can be determined. The concentration of the target constituent can then be determined from the determined current. This is illustrated, for example, in FIG. 5C, which is an exemplary plot of the voltage drop across the sense resistor 150 as constituent is added to the fluid sample during electrochemical operation. While shown in FIGS. 4A and 4B as disposed between the output of the first operational amplifier 140 and the first electrode 126, the sense resistor 150 can be positioned at any point in the current path (i.e., between the outputs of the first 140 and second 142 operational amplifiers) where the voltage drop thereacross can be measured. For example, in some embodiments, the sense resistor 150 can be coupled between the output of the second operational amplifier 142 and switch 133 while maintaining its functionality and operability.

In some embodiments, during the electrochemical process, the current flowing through the system can be largely attributed to the electrochemical reaction of the target constituent. The current caused by the electrochemical reaction is a measurement of the amount of charge per time received or given by the target constituent. In some embodiments, current additionally flows through the fluid sample 134 simply due to the sample's conductivity. However, often this current is much smaller than the electrochemical current and can be neglected and/or can be determined and subtracted from the measured electrochemical current.

In some embodiments, the sensor can be used to determine the sample conductivity with the switch 133 in position C as shown in FIG. 4A, coupling the output of the second operational amplifier 142 to the fourth electrode 132. Determination of the conductivity can be performed as described herein with regard to FIG. 4A. The switch 133 can be adjusted to position E as shown in FIG. 4B and an electrochemical measurement can be performed as described herein with regard to FIG. 4B. The measured conductivity of the fluid sample 134 can be used in an electrochemical concentration calculation, for example by subtracting any current expected to be flowing through the sample due to the voltage drop between electrodes across the conductive sample. In some embodiments, the conductivity and/or the concentration measurements and calculations are controlled by controller 155. In some configurations, controller 155 can perform a conductivity measurement, flip switch 133, perform a concentration measurements, and use the conductivity measurement in determining the concentration automatically.

Accordingly, switch 133 can be used to define the mode of operation of the controller. A user can position switch 133 in a first position (e.g., position C) or a second position (e.g., position E) for performing various methods of analysis, such as conductivity or electrochemical analysis. In some embodiments, user can position the switch via interface 156, which causes controller 155 to position the switch appropriately. The controller 155 can automatically position switch 133 in response to a command from a user to perform a particular measurement.

It should be noted that charge will generally not be transferred to or from the second electrode 128, since it is coupled to the high-impedance inverting inputs of the first operational amplifier 140. As such, fouling effects will not affect operation of the system at second electrode 128. First 126 and third 130 electrodes may be subject to fouling effects, however, in some embodiments, changes in sensor operation due to fouling, such as a change in applied voltage to effect the same current flow or electrochemical reaction, can provide information useful for detecting fouling on the sensor.

Figure 5D:
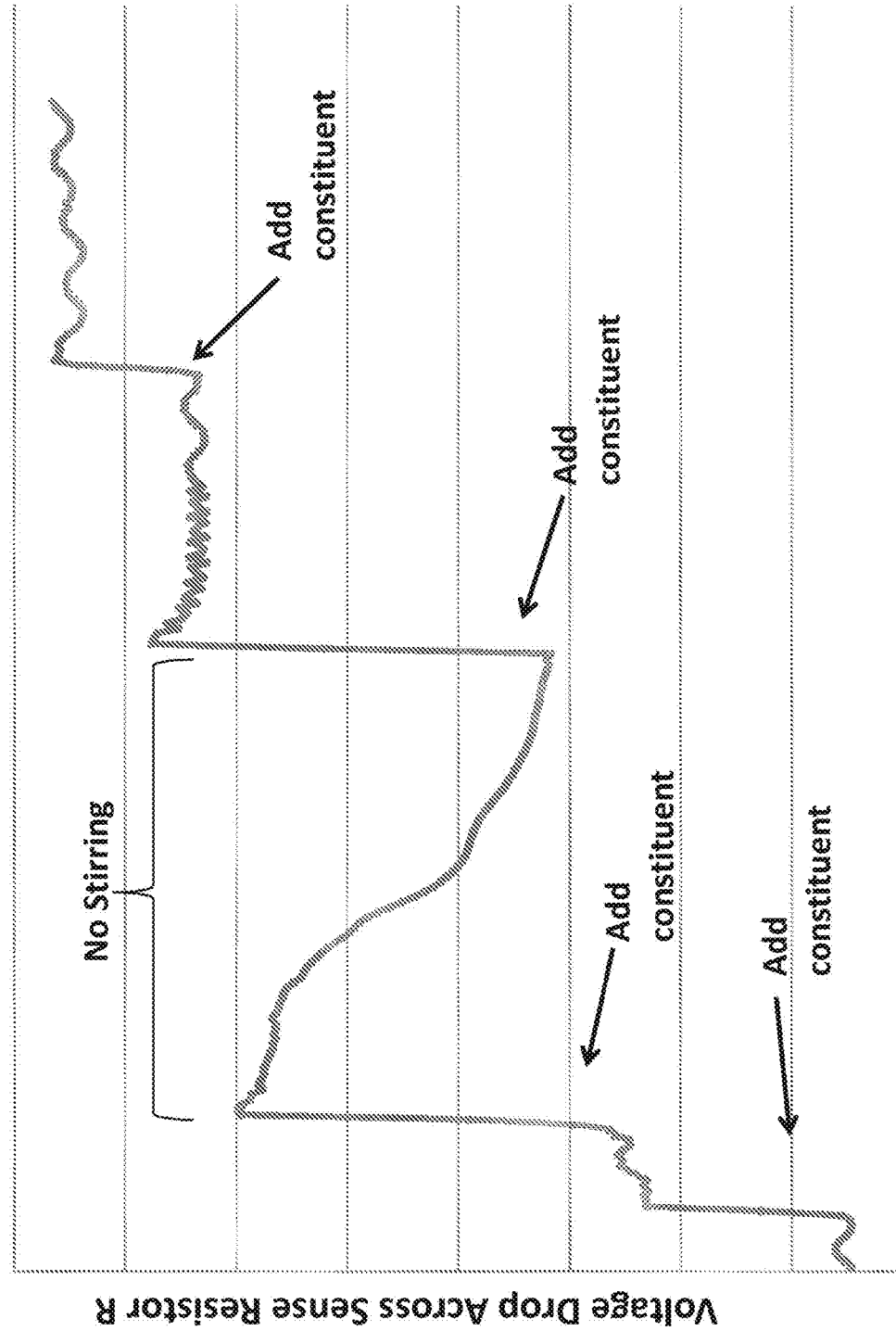

As discussed, the fluid sample 134 can be analyzed in line with a fluid system or can be isolated and analyzed independently. The fluid sample 134 can be analyzed while flowing or non-flowing in either case. When a flowing sample is used, fresh sample flows to the electrodes 126-132 throughout the analysis, and the electrochemical current will remain relatively constant. However, in embodiments in which a non-flowing sample is being analyzed, as the target constituent molecules proximate the electrodes undergo oxidation or reduction reactions, the remaining target constituent available to react can become depleted. As such, over time, the current flowing caused by the electrochemical reactions diminishes because of a lack of available target constituent. The process then becomes limited by diffusion of the target constituent through the fluid sample 134. Once the process is entirely limited by diffusion, the electrochemical reactions and current flow reach a steady state that is lower than that in the flowing sample. This can be seen, for example, in the exemplary plot of FIG. 5D, in which the measured voltage across the sense resistor 150, which is indicative of the current flowing in the sample, decreases over time when a sample is stagnant and no constituent is added.

In some embodiments, the electrochemical current data can be analyzed to determine the concentration of the target constituent. For example, integrating the current over time results in a calculation of total charge transferred over an amount of time. The total charge can be proportional to the number of molecules of target constituent that have electrochemically reacted, from which a concentration can be calculated. In some alternative embodiments, relationships between detected current and the concentration of a target constituent can be stored in a lookup table.

As has been described, various sample properties are utilized by the sensor to determine others. For example, in the case of non-flowing samples, the diffusion of a target constituent within a fluid sample can affect the rate of electrochemical reactions, which can in turn be used to determine the concentration of the target constituent. However, the diffusivity of a constituent through the sample fluid is not necessarily constant with temperature. Temperature dependence of various parameters can affect the outcome of measurements by the sensor, leading to inaccuracy in measurement.

Figure 6:
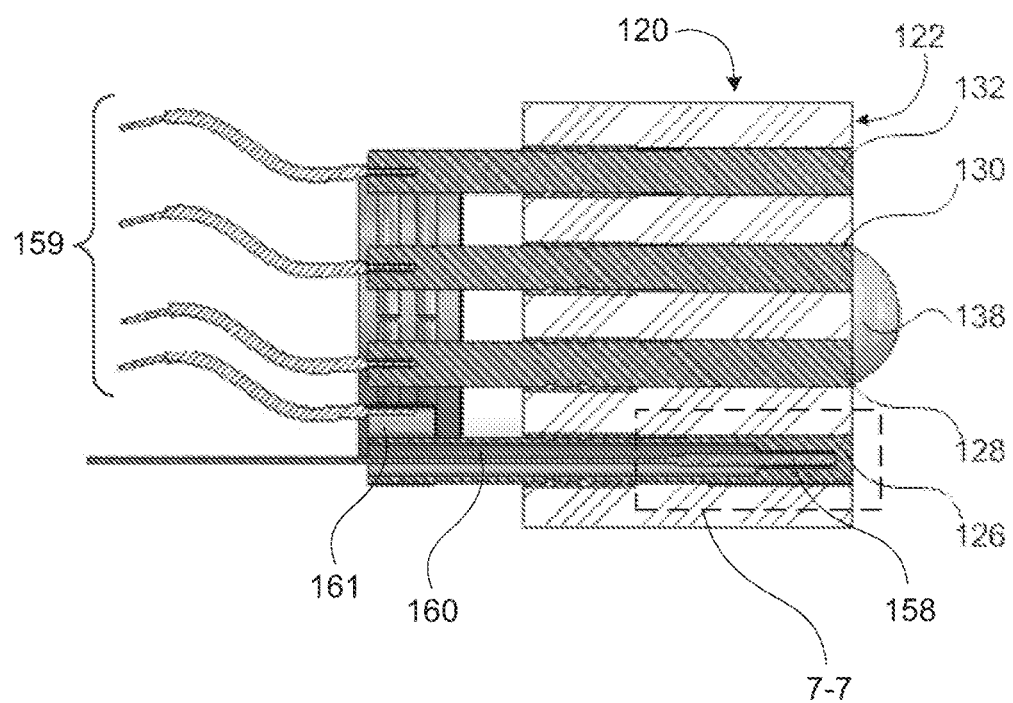
FIG. 6 is a cross-sectional view a first face of a housing comprising an electrode array, taken along line 6-6 in FIG. 3.

In some embodiments, the sensor comprises a temperature sensor for determining the temperature of the fluid sample. FIG. 6 is a cross-sectional view a first face of a housing comprising an electrode array, taken along line 6-6 in FIG. 3. FIG. 6 shows first 126, second 128, third 130 and fourth 132 electrodes extending through the first face 122 of the housing 120. In the illustrated embodiment, electrodes 126-132 are flush with the first face 122. Lens 138 is shown protruding from first face 122. In the embodiment of FIG. 6, the first electrode 126 comprises a bore 160 extending from a back surface of the first electrode 126 toward the first face 122. In some configurations, bore 160 can be shaped like an annular tube and be configured to house a temperature sensor 158, for example.

Temperature sensor 158 can be inserted into a bore 160 in the first electrode in order to measure the temperature of the fluid sample. In some embodiments, bore 160 extends only partially through the first electrode 126 and does not allow the temperature sensor 158 to contact the fluid sample directly. Instead, in some configurations, the first electrode 126 acts as the thermal conductor, in which the first electrode 126 is in thermal equilibrium with the fluid sample and the temperature sensor 158 measure the temperature of the fluid sample via the first electrode 126. Preventing contact between the temperature sensor 158 and the fluid sample can act to reduce wear or corrosion of the temperature sensor 158 by the fluid. In such configurations, embedding the temperature sensor in an electrode eliminates the requirement of an additional sealing surface on the sensor face 122. Temperature sensor 158 can include thermistors, thermocouples, resistance temperature detectors (RTD's), such as platinum RTD's, semiconductor temperature devices, or any other known temperature sensor. In some embodiments, when temperature sensor is an electrical sensor, preventing contact between the temperature sensor 158 and the fluid sample can act to electrically isolate the temperature sensor 158 from the fluid sample.

As shown in FIG. 6, electrodes 126-132 can be electrically coupled to circuitry (such as that shown in FIGS. 4A and 4B) by wires 159. Generally, wires 159 are shown as having bare ends disposed in the end of each electrode 126-132 opposite the first face 122. It will be appreciated that wires 159 can be electrically coupled to electrodes 126-132 in any number of configurations in order to prevent short circuiting the electrodes 126-132. In some embodiments, the first electrode 126 can include a conductive tab 161 for providing an interface between circuitry and the first electrode 126 while the first electrode 126 comprises a bore 160 for housing a temperature sensor 158. For example, a wire 159 for interfacing with the first electrode 126 can be embedded or otherwise in electrical communication with the conductive tab 161 on the first electrode 126. It should be appreciated that, while described in the illustrated embodiment as being incorporated into the first electrode 126, temperature sensor 158 can be disposed in a bore 160 in any of electrodes 126-132 in order to thermally communicate with the sample. A more detailed exemplary configuration between the temperature sensor and one of electrodes 126-132 is shown in FIG. 7.

Figure 7:
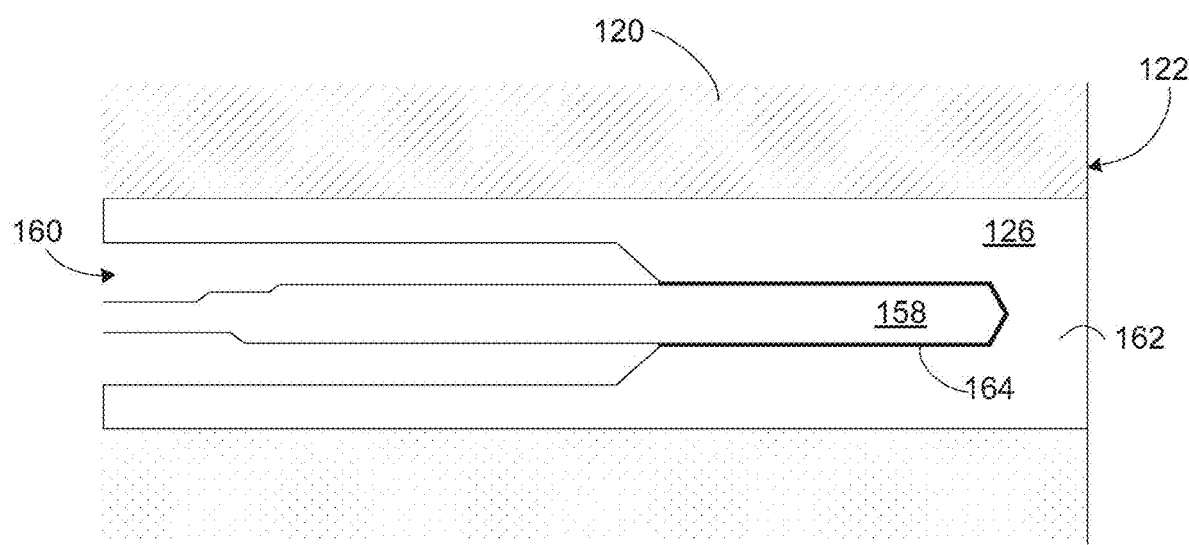
FIG. 7 is a view of a temperature sensor disposed in an electrode in an exemplary configuration such as in box 7-7 in FIG. 6.

FIG. 7 is a view of a temperature sensor disposed in an electrode in an exemplary configuration such as in box 7-7 in FIG. 6. FIG. 7 shows a first electrode 126 including a bore 160 along its longitudinal axis. First electrode 126 has a first end 162 having a surface flush with the first face 122 of a non-conductive housing 120. A temperature sensor 158 is shown disposed in the bore 160. In the illustrated embodiment, bore 160 extends toward the first end 162 of the first electrode 126, but does not extend to the surface flush with the first face 122. Temperature sensor 158 is positioned into the bore 160 so as to have a temperature sensing end proximate the first end 162 of the first electrode 126. In some embodiments, the bore 160 comprises an electrically insulating coating 164 to prevent unwanted electrical communication between the first electrode 126 and the temperature sensor 158. Electrically insulating coating 164 can comprise any appropriately insulating coating known. In some embodiments, the electrically insulating coating 164 is thermally conductive so as to place the temperature sensor 158 in thermal communication with the first electrode 126.

During operation, the first face 122 of the sensor housing 120 is disposed into a fluid sample. First electrode 126 contacts the fluid sample and changes temperature based on the temperature of the fluid sample. In some embodiments, the first end 162 of the first electrode 126 reaches thermal equilibrium with the fluid sample. The temperature sensor 158 disposed in the first end 162 of the first electrode 126 also reaches thermal equilibrium with the fluid sample and outputs temperature data indicative of the temperature. In some embodiments, the temperature sensor 158 is coupled to the controller 155 in order to communicate the temperature data thereto. Controller 155 can utilize temperature data while analyzing data, such as current data in a conductivity or electrochemical measurement, for example, in order to account for temperature-dependent parameters such as constituent diffusion.

Electrochemical and conductivity measurements have been described. Embodiments of the invention include sensors having a first face 122 having an electrode array 124 such as shown in FIG. 3. Electrodes 126-132 in the electrode array 124 can be coupled to a circuit arrangement as is shown in FIGS. 4A and 4B. Such a configuration allows the sensor to perform both conductivity and electrochemical measurements without manipulation of the sensor—the same arrangement can be used to perform either measurement. In some embodiments, the system comprises a controller 155 in communication with various components of the circuit in order to perform such measurements and process data. Embodiments of the system can include an interface 156 in communication with the controller 155. In some systems, for example, a user can initiate operation of the sensor, define and/or input parameters of the system, determine the mode of operation of the system, or receive information from the system via the interface 156.

In some embodiments, a user can initiate a fluid sample analysis procedure via interface 156. For example, a user can initiate a conductivity measurement, causing the controller 155 to communicate to the voltage source 146 to output an appropriate voltage Vi for a conductivity measurement. In some examples, Vi is between 0.1 and 0.2 volts for a conductivity measurement. During operation, the controller 155 can cause the switching mechanism 144 to toggle which non-inverting input is coupled to Vi and which to ground. In an exemplary embodiment, the controller 155 toggles two solid state switches at a frequency of 1 kHz, effectively applying a 1 kHz square wave between ground and Vi at each non-inverting input.

Controller 155 can additionally receive a signal from meter 154 indicative of the current flowing through the circuit and the fluid sample 134. In some embodiments, controller 155 can include a processor and memory for analyzing the signal received from meter 154. Controller 155 can process the received signal and utilize it to calculate the conductivity of the fluid sample 134. In an exemplary operation, a user communicates the resistance value of sense resistor 150 to the controller 155 via interface 156, and the controller utilizes the resistance value, the voltage Vi from voltage source 146, the received signal from the meter 154 and other known system parameters to determine the conductivity of the fluid sample 134. In some examples, various system parameters such as Vi and/or the value of the sense resistor 150 can be predetermined during construction of the system with values preprogrammed into controller 155. In such an example, a user can initiate a conductivity measurement via interface 156 and the controller 155 performs the measurement from predetermined operations and parameters stored in memory. In some embodiments, a user can select one or more parameters from a series of predetermined selectable options. After determining the conductivity of the fluid sample 134, in some configurations the controller 155 can further determine the concentration of various constituents in the sample, such as, for example, the combined concentration of ionized and soluble species in the fluid sample 134.

In some embodiments, a user can initiate electrochemical analysis of the fluid sample 134. As discussed elsewhere herein, various constituents of a sample electrochemically react at a variety of redox potentials. Accordingly, a user can select a target constituent having a corresponding known redox potential via the interface 156. In some embodiments, user can select the target constituent from a predetermined list. Upon selection, the controller 155 can cause the voltage source 146 to output an appropriate voltage to effect electrochemical reaction of the target constituent. An appropriate voltage can be stored in memory, such as in a lookup table based on the target constituent, for example. As discussed elsewhere herein, the electrochemical process can cause a current to flow through the fluid sample 134 and sense resistor 150. The controller 155 can receive a signal indicative of the flowing current from meter 154, and can use the current data to determine the concentration of the target constituent in the sample.

Figure 8:
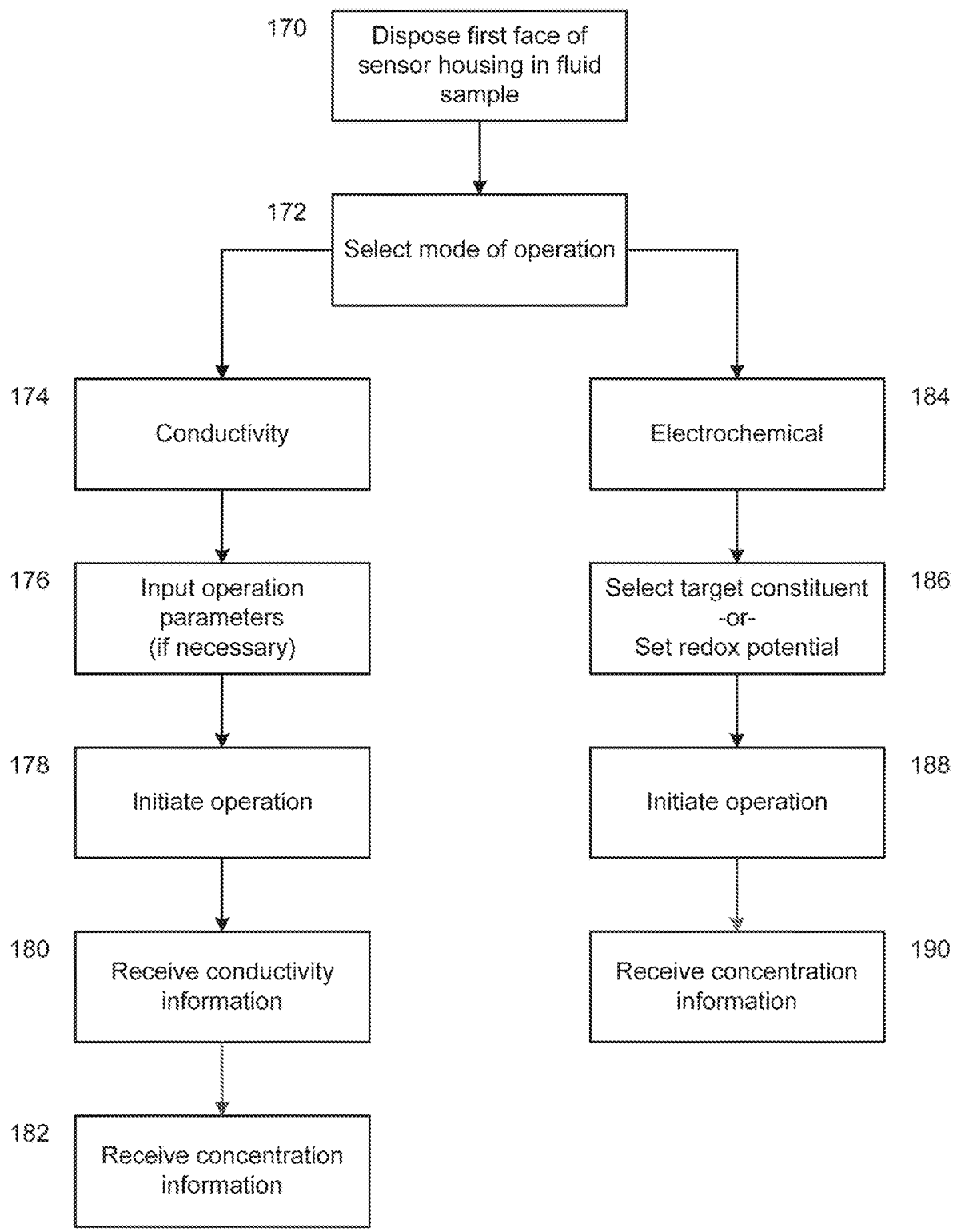
FIG. 8 is a process flow diagram illustrating exemplary operation of a sensor by a user.

Embodiments of the present invention include a method for using a sensor such as those herein described. FIG. 8 is a process flow diagram illustrating exemplary operation of a sensor by a user. A user can dispose 170 the first face of the sensor housing into a fluid sample to be analyzed. First face comprises electrodes electrically performing sample analysis. The user can select 172 a mode of operation of the sensor depending on the desired sample analysis. In some configurations, the step of selecting a mode of operation 172 can result in the positioning of switch 133 as in FIGS. 4A and 4B, enabling conductivity or electrochemical operation depending on the positioning of the switch.

The user can select conductivity 174 mode, and can input 176 any parameters that need to be defined. As described elsewhere herein, in some embodiments, user can select the value of an electrical potential applied to the fluid sample or the potential applied to an input of an amplifier that outputs to the fluid sample. A user may need to input the resistance value of a sense resistor used to measure current flow through the fluid sample. After inputting 176 any necessary parameters, a user can initiate 178 operation of the sensor. The user can then receive conductivity information 180 from the sensor based on the operation performed by the sensor. Conductivity information can include the actual conductivity of the sample, a determined resistance of the sample, the current flowing through the sample or any other information related to the conductivity measurement. In some embodiments, the user can alternatively or additionally receive concentration information 182 from the sensor. Concentration information can include the combined concentration of ionized and soluble species such as sanitizers, detergents, acids, and bases within the sample.

In other operations, user may select an electrochemical 184 mode of operation. As described elsewhere herein, during electrochemical operation, a user can select 186 a target constituent of the fluid sample to analyze. This selection will determine the electrical (redox) potential applied to the fluid sample from the sensor. In some cases, the user can set 186 the redox potential manually. Once the target constituent or redox potential is set, the user can initiate 188 operation of the sensor, causing the sensor to carry out a predetermined electrochemical operation based on the set parameters. After operation, the user can receive concentration information 190 from the sensor. Concentration information can include, for example, a measured current and/or the concentration of the target constituent in the fluid sample.

Figure 9:
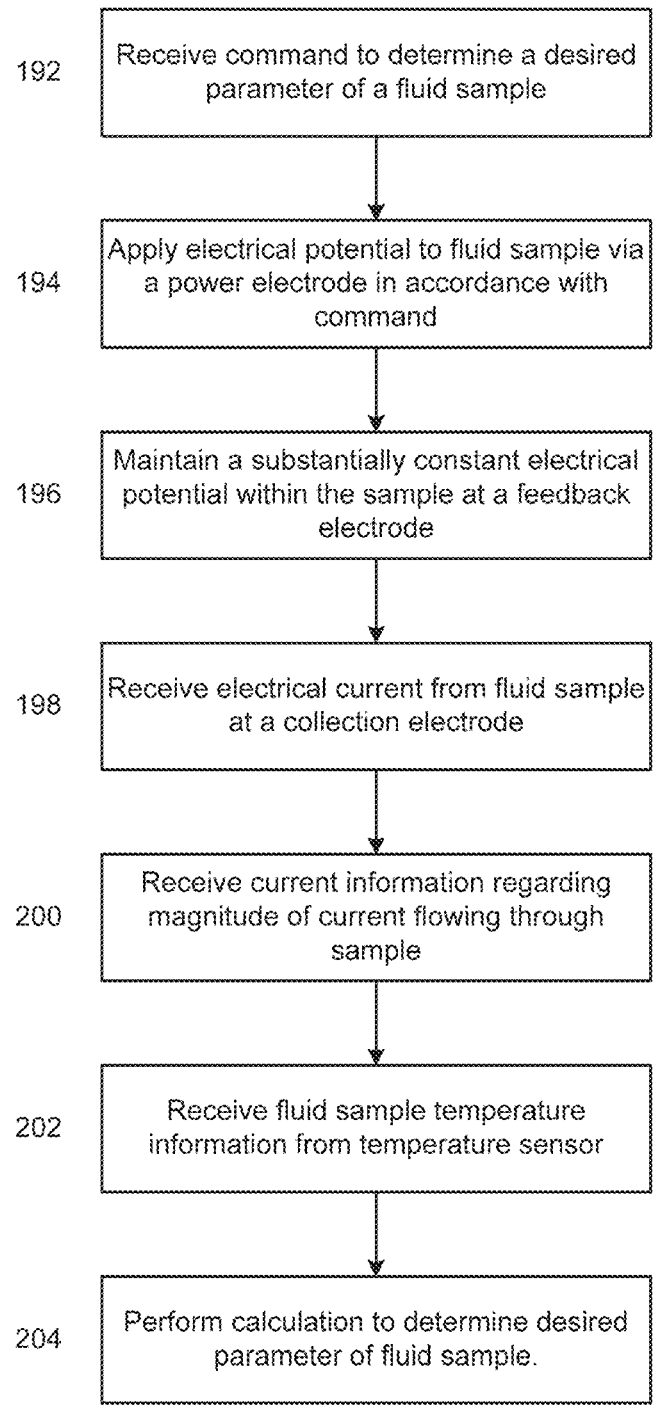
FIG. 9 is a process-flow diagram outlining an exemplary method to be performed by a sensor within a fluid analysis system in accordance with some aspects of the present invention.

Embodiments of the invention include methods performed by a component of or in communication with the sensor. FIG. 9 is a process-flow diagram outlining an exemplary method to be performed by a sensor within a fluid analysis system in accordance with some aspects of the present invention. Sensor can receive a command 192 to determine a desired parameter of a fluid sample. The command can be received from a user via an interface or an automated system configured to initiate analysis at a predetermined time, for example. The sensor can apply an electrical potential 194 to the fluid sample via a power electrode in accordance with the command. The nature of the applied electrical potential can depend on the received command. For example, in a conductivity measurement, the sensor can apply a low-magnitude, alternating current potential to the sample. During electrochemical analysis, however, sensor may apply a larger-magnitude, direct current potential to the sample. In some embodiments, the potential is applied to the sample relative to a reference ground applied to the sample at a separate electrode. In general, the power electrode can comprise either of first 126 or fourth 132 electrode.

In some embodiments, the sensor can maintain 196 a substantially constant electrical potential within the sample at a feedback electrode. Maintaining a substantially constant potential can include defining a reference ground or other reference potential within the sample. In some examples, the second 128 and third 130 electrodes can act as feedback electrodes for the sensor, which applies the necessary potential to the sample so as to maintain a constant potential at the feedback electrodes. Sensor can receive 198 electrical current at a collection electrode. Current can flow through the sample and collection electrode as a result of the applied electrical potential from the power electrode. The current detected at the collection electrode can be either positive or negative. That is, current can be flowing from the sample into the collection electrode, or from the collection electrode into the sample. As described with regard to various modes of operation, the collection electrode can comprise either the first electrode 126, the third electrode 130 (in electrochemical operation) or the fourth electrode 132 (in conductivity operation).

The sensor can receive current information 200 regarding the magnitude of the current flowing through the sample. In some examples, current flows through a sense resistor of a known resistance. In some examples, current information can comprise a voltage measured across the resistor which can be used to determine the flowing current. The voltage drop across the sense resistor is amplified by a differential amplifier, for example. In some embodiments, the sensor can receive fluid sample temperature information 202 from a temperature sensor. Various sample parameters that can affect the electrical properties of the fluid sample can be dependent upon the sample temperature. The sensor can perform a calculation to determine 204 a desired parameters of the fluid sample. Determining 204 can be done based on any or all of the applied electrical potential, the received current information and the received temperature information. In various embodiments, desired parameter can comprise the conductivity of the sample, the concentration of a target constituent of the fluid sample, or the combined concentration of ionized and soluble species in a fluid sample, for example.

The exemplary method of FIG. 9 can be carried out, for example, by a controller as a part of or in communication with the sensor. Controllers may include processors, such as microprocessors, digital signal processors (DSPs), application specific integrated circuits (ASICs), field programmable gate arrays (FPGAs), or any other equivalent integrated or discrete logic circuitry, as well as any combinations of such components. In some embodiments, methods such as that illustrated in FIG. 9 can be encoded as instructions programmed in a non-transitory computer-readable medium for causing a programmable processor to carry out the method in response to a received command.

Various systems, sensors and methods have been described. Such examples are non-limiting, and do not define or limit the scope of the invention in any way. Rather, these and other examples are within the scope of the following claims.

The invention claimed is:

1. A non-transitory computer-readable medium containing executable instructions for determining a value of a predetermined parameter of a fluid sample via a sensor that includes:
   a non-conductive housing having a first face,
   an operational amplifier,
   an electrode array mounted in the first face of the non-conductive housing and comprising a first electrode, a fourth electrode, a second electrode disposed between the first electrode and the fourth electrode, and a third electrode disposed between the second electrode and the fourth electrode, the third electrode being coupled to an input of the operational amplifier; and
   a first switch coupled to an output of the operational amplifier; and
   the non-transitory computer-readable medium comprising instructions for causing a programmable processor to:
      receive a command initiating a mode of operation;
      position the first switch in either a first position or a second position based on the received command; wherein
         in the first position, the switch couples the output of the operational amplifier to the fourth electrode; and
         in the second position, the switch couples the output of the operational amplifier to the third electrode;
      apply an electrical potential to the fluid sample via the first electrode;
      maintain a substantially constant electrical potential within the fluid sample via at least one of the second electrode and the third electrode;
      receive an electrical current flowing through the fluid sample at the fourth electrode;
      receive current information providing an indication of the magnitude of the current flowing through the fluid sample;
      perform a calculation using the applied electrical potential and received current information to determine the value of the predetermined parameter of the fluid sample.

2. The non-transitory computer-readable medium of claim 1, further comprising instructions for causing the programmable processor to receive fluid sample temperature information from a temperature sensor; and wherein performing the calculation comprises using the fluid sample temperature information to determine the value of the predetermined parameter of the fluid sample.

3. The non-transitory computer-readable medium of claim 1, wherein the desired parameter of the fluid sample is one in the group consisting of: the conductivity of the fluid sample, the concentration of a target constituent in the fluid sample, and the combined concentration of ionized and soluble species in the fluid sample.

4. The non-transitory computer-readable medium of claim 1, wherein receiving current information comprises receiving a signal indicative of a voltage drop across a known resistor.

5. The non-transitory computer-readable medium of claim 4, wherein applying the electrical potential to the fluid sample comprises applying an alternating current potential.

6. The non-transitory computer-readable medium of claim 5, wherein performing the calculation comprises calculating the conductivity of the fluid sample.

7. The non-transitory computer-readable medium of claim 5, wherein applying the alternating current potential to the fluid sample comprises controlling at least a second switch coupled to a direct current voltage source to produce a substantially square wave to apply to the fluid sample.

8. The non-transitory computer-readable medium of claim 7, wherein:
the received signal indicative of the voltage drop across the known resistor comprises two values, each value corresponding to a voltage drop in a different direction across the known resistor; and
performing the calculation comprises calculating the difference between the two values in the received signal.

9. The non-transitory computer-readable medium of claim 1, wherein the programmable processor is configured to receive a command to determine a desired parameter of the fluid sample; and wherein
the applied electrical potential is dependent upon the received command.

10. The non-transitory computer-readable medium of claim 9, wherein the received command is selected from a list of predefined commands.

11. The non-transitory computer-readable medium of claim 10, wherein the received command comprises determining the concentration of a target constituent in the fluid sample; and wherein
the applied electrical potential relative to the substantially constant electrical potential at the at least one of the second electrode and the electrode comprises a predetermined redox potential of the target constituent.

12. The non-transitory computer-readable medium of claim 11, wherein the target constituent comprises one of the group consisting of: peroxides, peracids, and hypochlorite.

13. The non-transitory computer-readable medium of claim 4, wherein applying the electrical potential to the fluid sample comprises applying a direct current potential.

14. A non-transitory computer-readable medium containing executable instructions for determining a value of a predetermined parameter of a fluid sample, the medium comprising instructions for causing a programmable processor to:
receive a command initiating a mode of operation of a sensor, the sensor comprising:
an operational amplifier;
a first electrode, a second electrode, a third electrode and a fourth electrode; wherein
the second electrode is disposed between the first electrode and the fourth electrode, and
the third electrode is disposed between the second electrode and the fourth electrode and is coupled to an input of the operational amplifier; and
a switch;
position the switch based on the received command in either a first position or a second position; wherein
in the first position, the switch couples an output of the operational amplifier to the forth electrode; and
in the second position, the switch couples the output of the operational amplifier to the third electrode; and wherein
the switch is positioned in the first position in the event of a first mode of operation being received via the received command; and
the switch is positioned in the second position in the event of a second mode of operation being received via the received command.

15. The non-transitory computer-readable medium of claim 14, wherein the first mode of operation comprises a conductivity mode of operation.

16. The non-transitory computer-readable medium of claim 15, wherein receiving the command initiating the mode of operation of the sensor comprising receiving a selection of the first mode of operation, and wherein the medium further comprises instructions for causing the programmable processor to:
initiate a conductivity analysis of the fluid sample; and
generate information comprising:
information indicative of the conductivity of the fluid sample; and/or
information indicative of the combined concentration of ionized and soluble species in the fluid sample.

17. The non-transitory computer-readable medium of claim 14, wherein the second mode of operation comprises an electrochemical mode of operation.

18. The non-transitory computer-readable medium of claim 17, wherein receiving the command initiating the mode of operation of the sensor comprises receiving a selection of the second mode of operation, and wherein the medium further comprises instructions for causing the programmable processor to:
initiate an electrochemical analysis of the fluid sample; and
receive a selection of a target constituent of the fluid sample; and
provide an electrical potential to the fluid sample to effect an electrochemical reaction of the target constituent in the fluid sample based on the received selection of the target constituent.

\* \* \* \* \*